United States Patent [19]
Place

[11] Patent Number: 5,925,629
[45] Date of Patent: Jul. 20, 1999

[54] TRANSURETHRAL ADMINISTRATION OF ANDROGENIC AGENTS FOR THE TREATMENT OF ERECTILE DYSFUNCTION

[75] Inventor: Virgil A. Place, Kawaihae, Hi.

[73] Assignee: VIVUS, Incorporated, Mountain View, Calif.

[21] Appl. No.: 08/959,243

[22] Filed: Oct. 28, 1997

Related U.S. Application Data

[51] Int. Cl.⁶ ..................................................... A61K 31/56
[52] U.S. Cl. ................................................................ 514/179
[58] Field of Search ............................................... 514/179

[56] References Cited

U.S. PATENT DOCUMENTS

| | | | |
|---|---|---|---|
| 4,478,822 | 10/1984 | Haslam et al. | 424/78 |
| 4,610,868 | 9/1986 | Fountain et al. | 424/1.1 |
| 4,801,587 | 1/1989 | Voss et al. | 514/248 |
| 4,863,970 | 9/1989 | Patel et al. | 514/784 |
| 5,242,391 | 9/1993 | Place et al. | 604/60 |
| 5,342,834 | 8/1994 | Bardin et al. | 514/178 |
| 5,474,535 | 12/1995 | Place et al. | 604/60 |
| 5,518,499 | 5/1996 | Agar | 600/40 |
| 5,646,181 | 7/1997 | Fung et al. | 514/506 |

FOREIGN PATENT DOCUMENTS

| | | |
|---|---|---|
| 0357581 | 3/1990 | European Pat. Off. |
| WO91/16021 | 10/1991 | WIPO |
| WO94/22460 | 10/1994 | WIPO |
| WO95/09006 | 4/1995 | WIPO |
| WO95/26158 | 10/1995 | WIPO |

OTHER PUBLICATIONS

Lugg et al, Chemical Abstracts, vol. 122, abstract No. 205525, 1995.
Garban et al, Chemical Abstracts, vol. 123, abstract No. 330351, 1995.
Gray et al, Chemical Abstracts, vol. 92, abstract No. 191771, 1980.
Guinan et al, Medline Abstracts, abstract No. 76203666, 1976.
Basile et al. (1994), "Medical Treatment of Neurogenic Impotence," *Sexuality and Disability* 12(1):81–94.
Mills et al. (1996), "Sites of Androgenic Regulation of Cavernosal Blood Pressure During Penile Erection in the Rat," *International Journal of Impotence Research* 8:29–34.

*Primary Examiner*—William R. A. Jarvis
*Attorney, Agent, or Firm*—Dianne E. Reed; Bozicevic & Reed LLP

[57] ABSTRACT

A method is provided for treating erectile dysfunction in an individual. The method involves the administration of an androgenic steroid within the context of an effective dosing regimen. The preferred mode of administration is transurethral; however, the selected inhibitor may also be delivered via intracavernosal injection or using alternative routes. Pharmaceutical formulations and kits are provided as well.

26 Claims, 1 Drawing Sheet

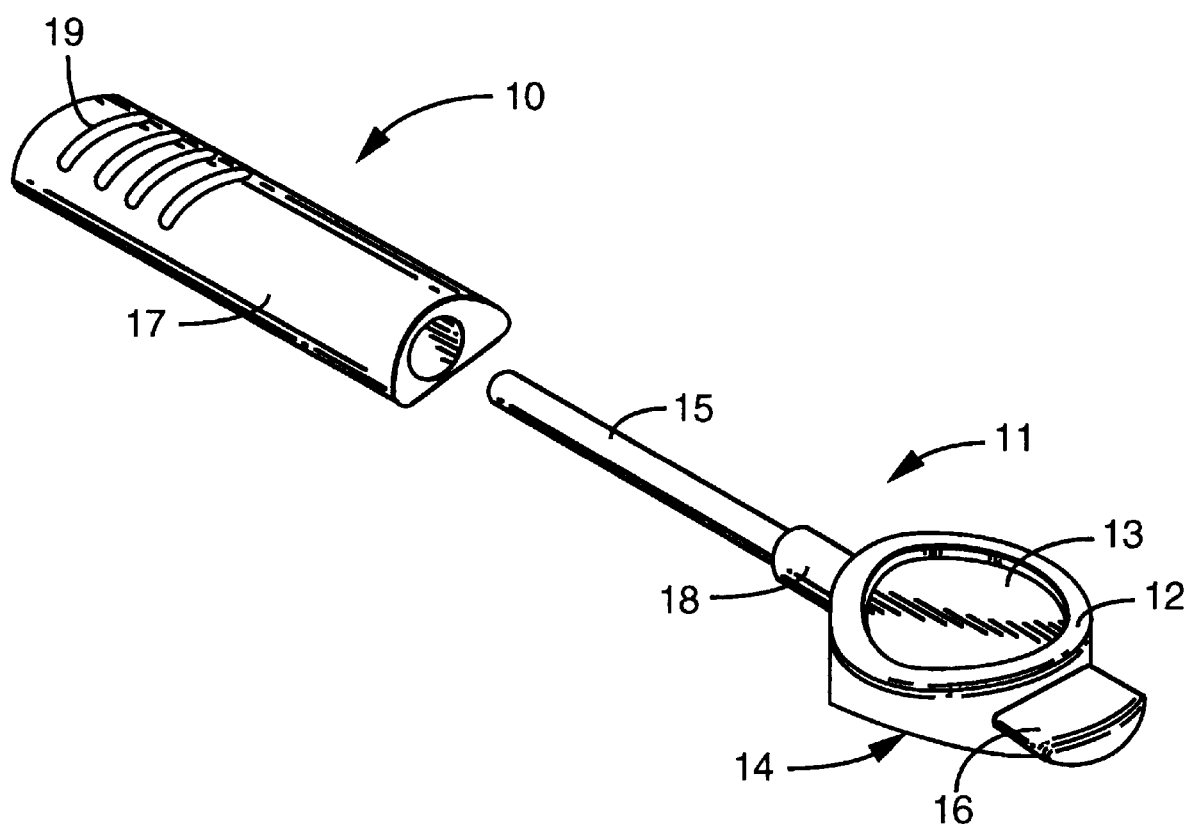

TRANSURETHRAL ADMINISTRATION OF ANDROGENIC AGENTS FOR THE TREATMENT OF ERECTILE DYSFUNCTION

TECHNICAL FIELD

This invention relates generally to methods and pharmaceutical compositions for treating erectile dysfunction; more particularly, the invention relates to the transurethral administration of androgenic agents to treat erectile dysfunction.

BACKGROUND

Impotence is the consistent inability to achieve or sustain an erection of sufficient rigidity for sexual intercourse. It has recently been estimated that approximately 10 million American men are impotent (R. Shabsigh et al., "Evaluation of Erectile Impotence," *Urology* 32:83–90 (1988); W. L. Furlow, "Prevalence of Impotence in the United States," *Med. Aspects Hum. Sex.* 19:13–6 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male*; A. C. Kinsey et al., eds., Philadelphia, Pa.: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87-1751). Depending on the nature and cause of the problem, treatments include psychosexual therapy, hormonal therapy, administration of vasodilators such as nitroglycerin and α-adrenergic blocking agents ("α-blockers"), oral administration of other pharmaceutical agents, vascular surgery, implanted penile prostheses, vacuum constriction devices and external aids such as penile splints to support the penis or penile constricting rings to alter the flow of blood through the penis.

A number of causes of impotence have been identified, including vasculogenic, neurogenic, endocrinologic and psychogenic.

Vasculogenic impotence, which is caused by alterations in the flow of blood to and from the penis, is thought to be the most frequent organic cause of impotence. Common risk factors for vasculogenic impotence include hypertension, diabetes, cigarette smoking, pelvic trauma, and the like.

Neurogenic impotence is associated with spinal-cord injury, multiple sclerosis, peripheral neuropathy caused by diabetes or alcoholism and severance of the autonomic nerve supply to the penis consequent to prostate surgery.

Erectile dysfunction is also associated with disturbances in endocrine function resulting in low circulating testosterone levels and elevated prolactin levels.

Impotence can also be a side effect of various classes of drugs, in particular, those that interfere with central neuroendocrine control or local neurovascular control of penile smooth muscle. Krane et al., *New England Journal of Medicine* 321:1648 (1989). Penile erection requires (1) dilation of the arteries that regulate blood flow to the lacunae of the corpora cavernosum, (2) relaxation of trabecular smooth muscle, which facilitates engorgement of the penis with blood, and (3) compression of the venules by the expanding trabecular walls to decrease venous outflow.

Trabecular smooth muscle tone is controlled locally by adrenergic (constrictor), cholinergic (dilator) and nonadrenergic, noncholinergic (dilator) innervation, and by endothelium-derived vasoactive substances such as vasoactive intestinal polypeptide (VIP), prostanoids, endothelin and nitrous oxide. High sympathetic tone (noradrenergic) is implicated in erectile dysfunction, and, in some patients, the disorder can be successfully treated with noradrenergic receptor antagonists. See, e.g., Krane et al., supra.

There is also evidence that dopaminergic mechanisms are involved in erectile function. For example, pharmacologic agents that elevate the level of brain dopamine or stimulate brain dopamine receptors increase sexual activity in animals (see, e.g., Gessa & Tagliamonte, *Life Sciences* 14:425 (1974); Da Prada et al., *Brain Research* 57:383 (1973)).

Administration of L-DOPA, a dopamine precursor, enhances sexual activity in male rats. L-DOPA has been used in the treatment of Parkinsonism and is known to act as an aphrodisiac in some patients (Gessa & Tagliamonte, supra; Hyppa et al., *Acta Neurologic Scand.* 46:223 (Supp. 43, 1970)). Specific dopamine agonists have been studied for their effects on erectile function. Apomorphine, (n-propyl) norapomorphine, bromocriptine, amantidine, fenfluramine, L-DOPA and various other pharmacological activators of central dopaminergic receptors have been found to increase episodes of penile erection in male rats (Benassi-Benelli et al., *Arch. int. Pharmacodyn.* 242:241 (1979); Poggioli et al., *Riv. di Farm. & Terap.* 9:213 (1978); Falaschi et al., *Apomorphine and Other Dopaminomimetics*, 1:117–121 (Gessa & Corsini, Eds., Raven Press, N.Y.)). In addition, U.S. Pat. No. 4,521,421 to Foreman relates to the oral or intravenous administration of quinoline compounds to treat sexual dysfunction in mammals.

The currently available dopamine agonists, with few exceptions, have found limited use in the treatment of erectile dysfunction because of their peripheral side effects. These effects include nausea and vomiting, postural hypotension, arrhythmias, tachycardia, dysphoria, psychosis, hallucinations, drowsiness and dyskinesias (See, e.g., Martindale *The Extra Pharmacopoeia*, 31st Ed., pages 1151–1168).

The invention described herein provides a means to avoid the above-mentioned side effects in administering suitable active agents in treating erectile dysfunction. Specifically, the invention relates to methods, pharmaceutical compositions and kits for treating erectile dysfunction, particularly vasculogenic erectile dysfunction. The invention involves transurethral administration of an androgenic agent as will be described in detail herein.

T. M. Mills et al., "Sites of Androgenic Regulation of Cavernosal Blood Pressure During Penile Erection in the Rat," *International Journal of Impotence Research* 8:29–34 (1996), investigates the role of androgens in regulating erectile blood flow, and proposes a model for further experiments concerning control of the erectile response in rats and other species. U.S. Pat. No. 5,342,834 to Bardin et al. also pertains to androgenic agents and erectile dysfunction, and suggests the administration of androgenic agents "for providing androgen hormone supplementation" such as in the treatment of impotence and infertility. Neither reference discloses or suggests transurethral administration of androgenic or other agents to treat erectile dysfunction.

Transurethral administration of pharmacologically active agents has been described. U.S. Pat. No. 4,478,822 to Haslam et al. relates to a controlled release, thermosetting gel formulation for delivering drugs into a body cavity such as the urethra. U.S. Pat. No. 4,610,868 to Fountain et al. describes a biodegradable lipid matrix composition for administering a drug, optionally through the urethra. Basile et al., "Medical Treatment of Neurogenic Impotence," *Sexual Disabilities* 12(1):81–94 (1994) describes the intraurethral administration of drugs. While these references mention urethral drug delivery, the potential importance of administering androgenic agents in this manner, to treat erectile dysfunction, is unknown. Applicant is unaware of any art disclosing the effectiveness of transurethral administration of androgenic agents such as testosterone, or testosterone derivatives or analogs, in the treatment or prevention of impotence.

In addition to the aforementioned references, the following documents are of interest insofar as they relate to urethral drug delivery: International Patent Publication No. WO91/16021; U.S. Pat. No. 4,801,587 to Voss et al.; and U.S. Pat. No. 5,242,391 to Place et al. These references relate to the treatment of erectile dysfunction by delivering a vasoactive agent into the male urethra.

The following documents are also of interest insofar as they relate to the treatment of erectile dysfunction by delivering a vasoactive agent locally to the penis.

U.S. Pat. No. 4,127,118 to Latorre describes the injection of vasodilator drugs into the corpora cavemosa of the penis to dilate the arteries that supply blood to the erectile tissues, thereby inducing an erection.

U.S. Pat. No. 5,439,938 to Snyder et al. describes the administration of nitric oxide (NO) synthase inhibitors by direct injection of a drug into the corpora cavemosa, by topical drug administration or transurethral drug administration, for inhibiting penile erection due to priapism and for treating urinary incontinence.

Virag et al., *Angiology-Journal of Vascular Diseases* (February 1984), pp. 79–87, Brindley, *Brit. J. Psychiat.* 143:332–337 (1983) and Stief et al., *Urology* XXXI:483–485 (1988) respectively describe the intracavernosal injection of papaverine (a smooth muscle relaxant), phenoxybenzamine or phentolamine (α-receptor blockers) and a phentolamine-papaverine mixture to treat erectile dysfunction.

It has now been discovered that transurethral administration of androgenic agents, as provided herein, is extremely effective in the prevention and treatment of erectile dysfunction. While not wishing to be bound by theory, applicant hypothesizes that the high local levels of active agent which are achieved by the present method provide for unexpected success in addressing the problem of male erectile dysfunction, particularly vasculogenic impotence.

SUMMARY OF THE INVENTION

Accordingly, it is a primary object of the invention to prove a method for treating erectile dysfunction by transurethrally administering an effective amount of a selected androgenic agent to an individual in need of such therapy.

It is another object of the invention to provide such a method wherein the androgenic agent is contained in a transurethral dosage form and administered within the context of a dosing regimen effective to treat erectile dysfunction.

It is still another object of the invention to provide such a method in which the androgenic agent is administered in conjunction with a transurethral permeation enhancer.

It is yet another object of the invention to provide a pharmaceutical composition for carrying out the aforementioned method.

It is a further object of the invention to provide a kit capable of use by an individual in carrying out the aforementioned method.

Additional objects, advantages and novel features of the invention will be set forth in part in the description which follows, and in part will become apparent to those skilled in the art upon examination of the following, or may be learned by practice of the invention.

In a first aspect of the invention, a method is provided for treating erectile dysfunction in an individual prone to erectile dysfunctionl, particularly vasculogenic erectile dysfunction, the method comprising administering to the urethra of the individual a pharmaceutical composition containing an androgenic agent. The composition is provided as a urethral dosage form such as, for example, a urethral suppository. Administration of the pharmaceutical composition is carried out within the context of a dosing regimen such that the agent is effective in the treatment of erectile dysfunction. The method is especially useful in the treatment of vasculogenic impotence, although other types of erectile dysfunction may also be treated using the present formulations.

In another aspect of the invention, a pharmaceutical composition is provided for treating erectile dysfunction. The pharmaceutical composition comprises an effective amount of an androgenic agent, preferably testosterone or a derivative or analog thereof, a carrier or vehicle suitable for transurethral drug delivery, and, optionally, a transurethral permeation enhancer. Other types of components may be incorporated into the composition as well, e.g., excipients, surfactants, preservatives (e.g., antioxidants), stabilizers, chelating agents, enzyme inhibitors, antibacterial agents and the like, as will be appreciated by those skilled in the art of drug formulation preparation and delivery. The composition is specifically formulated for urethral administration.

In another aspect of the invention, a kit is provided to assist an individual in transurethral drug administration. Generally, the kit includes the following components: a pharmaceutical composition comprising the androgenic agent to be administered; a device for effecting transurethral delivery of the pharmaceutical composition; a container housing the composition during storage and prior to use; and written instructions for carrying out drug administration in a manner effective to treat erectile dysfunction.

BRIEF DESCRIPTION OF THE DRAWING

FIG. 1 is an exploded view of one embodiment of a transurethral therapeutic device which may be used in conjunction with the present method.

DETAILED DESCRIPTION OF THE INVENTION

Definitions:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "an androgenic agent" includes a mixture of two or more such agents, reference to "a permeation enhancer" includes mixtures of two or more enhancers, and the like.

In describing and claiming the present invention, the following terminology will be used in accordance with the definitions set out below.

The terms "active agent," "drug" and "pharmacologically active agent" are used interchangeably herein to refer to a chemical material or compound that induces a desired effect. In the context of the present invention, the terms refer to an androgenic agent.

The terms "transurethral," "intraurethral" and "urethral" to specify the preferred mode of administration herein are used interchangeably to refer to the delivery of the drug into the urethra such that drug contacts and passes through the wall of the urethra. As noted elsewhere herein, the present method preferably involves delivery of the drug at least about 3 cm and preferably at least about 7 cm into the urethra.

The term "erectile dysfunction" is intended to include any and all types of erectile dysfunction, including: vasculogenic, neurogenic, endocrinologic and psychogenic impotence ("impotence" is used here in its broadest sense to indicate an inability a periodic or consistent inability to achieve or sustain an erection of sufficient rigidity for sexual intercourse; see U.S. Pat. No. 5,242,391 to Place et al., cited supra); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, *Disorders of Sexual Desire* (New York, N.Y.: Brunner Mazel Book Inc., 1979)).

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. The present method of "treating" erectile dysfunction, as the term is used herein, thus encompasses both prevention of the disorder in a predisposed individual and treatment of the disorder in a clinically symptomatic individual.

"Penetration enhancement" or "permeation enhancement" as used herein relates to an increase in the permeability of the urethral wall to the selected pharmacologically active agent, i.e., so that the rate at which the drug permeates through the urethral wall is increased.

"Carriers" or "vehicles" as used herein refer to carrier materials suitable for drug administration, which is preferably either transurethral or via injection into the penile cavernosal tissues. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect, i.e., treatment of erectile dysfunction.

Active Agents for Treatment of Erectile Dysfunction:

In order to carry out the method of the invention, a selected androgenic agent is administered to the urethra of an individual prone to erectile dysfunction. Suitable androgenic agents include, but are not limited to: the naturally occurring androgens androsterone, testosterone, dehydroepiandrosterone (DHEA), and dihydrotestosterone (DHT); pharmaceutically acceptable esters of testosterone and dihydrotestosterone, typically esters formed from the hydroxyl group present at the C-17 position, including, but not limited to, the enanthate, propionate, cypionate, phenylacetate, acetate, buciclate, heptanoate, decanoate, undecanoate, caprate, isocaprate, esters; and pharmaceutically acceptable derivatives of testosterone such as methyltestosterone, testolactone, oxymetholone and fluoxymesterone. Testosterone and the 17-esters thereof, particularly the enanthate, propionate and cypionate esters, are preferred. These compounds are sometimes collectively referred to herein as "testosterone and derivatives and analogs thereof."

The androgenic agent may be administered in the form of a pharmaceutically acceptable salt, as will be appreciated by those skilled in the art. Salts may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

For example, acid addition salts are prepared from the free base using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids.

Conversely, preparation of basic salts of acid moieties which may be present on the active agent are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts.

Pharmaceutical Compositions and Administration Thereof:

The active agent is administered in a pharmaceutical composition suitable for transurethral drug delivery. The composition contains one or more selected carriers excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

It is preferred that the pharmaceutical compositions contain one or more transurethral permeation enhancers, i.e., compounds which act to increase the rate at which the selected drug permeates through the urethral membrane. Examples of suitable permeation enhancers include dimethylsulfoxide ("DMSO"), dimethyl formamide ("DMF"), N,N-dimethylacetamide ("DMA"), decylmethylsulfoxide ("$C_{10}MSO$"), polyethylene glycol monolaurate ("PEGML"), glycerol monolaurate, lecithin, the 1-substituted azacycloheptan-2-ones, particularly 1-n-dodecylcyclaza-cycloheptan-2-one (available under the trademark Azone® from Nelson Research & Development Co., Irvine, Calif.), SEPA® (available from Macrochem Co., Lexington, Mass.), alcohols (e.g., ethanol), surfactants as discussed above, including, for example, Tergitol®, Nonoxynol-9® and TWEEN-80®, and lower alkanols such as ethanol.

Transurethral formulations may additionally include one or more enzyme inhibitors effective to inhibit drugdegrading enzymes which may be present in the urethra. Such enzyme inhibiting compounds may be determined by those skilled in the art by reference to the pertinent literature and/or using routine experimental methods. Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration, as explained in co-pending patent application Ser. No. 07/514,397, entitled "Treatment of Erectile Dysfunction" published internationally as WO 91/16021), can be carried out in a number of different ways using a variety of urethral dosage forms. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. A preferred drug delivery device for administering a drug transurethrally is shown in FIG. 1. It is preferred, although not essential, that the drug be delivered at least about 3 cm into the urethra, and preferably at least about 7 cm into the urethra. Generally, delivery at about 3 cm to about 8 cm into the urethra will provide effective results in conjunction with the present method.

Urethral suppository formulations containing PEG or a PEG derivative are particularly preferred urethral dosage forms herein, and may be conveniently formulated using conventional techniques, e.g., compression molding, heat molding or the like, as will be appreciated by those skilled in the art and as described in the pertinent literature and pharmaceutical texts. See, for example, *Remington: The Science and Practice of Pharmacy*, 19th Ed. (Easton, Pa.: Mack Publishing Co., 1995), which discloses typical methods of preparing pharmaceutical compositions in the form of urethral suppositories. The PEG or PEG derivative preferably has a molecular weight $M_w$ in the range of about 200 to 2500, more preferably in the range of about 1000 to 2000. Suitable polyethylene glycol derivatives include polyethylene glycol fatty acid esters, for example, polyethylene glycol monostearate, polyethylene glycol sorbitan esters, e.g., polysorbates, and the like. It is also preferred that urethral suppositories contain one or more solubilizing agents effective to increase the solubility of the active agent in the transurethral vehicle and the bioavailability of the drug.

The solubilizing agent may be a nonionic, anionic, cationic or amphoteric surfactant. Nonionic surfactants include: long-chain fatty acids, i.e., acids having the structural formula $CH_3(CH_2)_m COOH$ where m is an integer in the range of 8 to 16; fatty alcohols, that is, alcohols having the structural formula $CH_3(CH_2)_m C(H)OH$, such as lauryl, cetyl and stearyl alcohols; glyceryl esters such as the naturally occurring mono-, di- and triglycerides; and esters of fatty alcohols or other alcohols such as propylene glycol, polyethylene glycol, sorbitan, sucrose, and cholesterol. Examples of water-soluble nonionic surfactant derivatives include sorbitan fatty acid esters (such as those sold under the tradename Span®), polyoxyethylene sorbitan fatty acid esters (such as those sold under the tradename TWEEN®), polyoxyethylene fatty acid esters (such as those sold under the tradename Myrj®), polyoxyethylene steroidal esters, polyoxypropylene sorbitan fatty acid esters, polyoxypropylene fatty acid esters, polyoxypropylene steroidal esters, polyoxyethylene ethers (such as those sold under the tradename Brij®), polyglycol ethers (such as those sold under the tradename Tergitol®), and the like. Preferred nonionic surfactants for use as the solubilizing agent herein are polyglycol ether, polyoxyethylene sorbitan trioleate, sorbitan monopalmitate, polysorbate 80, polyoxyethylene 4-lauryl ether, propylene glycol, and mixtures thereof. Anionic surfactants which may be used as the solubilizing agent herein include long-chain alkyl sulfonates, carboxylates, and sulfates, as well as allyl aryl sulfonates, and the like. Preferred anionic surfactants are sodium dodecyl sulfate, dialkyl sodium sulfosuccinate (e.g., sodium bis-(2-ethylhexyl)-sulfosuccinate), sodium 7-ethyl-2-methyl-4-docyl sulfate and sodium dodecylbenzene sulfonate. Cationic surfactants which may be used to solubilize the active agent are generally long-chain amine salts or quaternary ammonium salts, e.g., decyltrimethylammonium bromide, dodecyltriethylammonium bromide, tetradecyltrimethylammonium bromide, tetradecyltrimethylammonium chloride, and the like. Amphoteric surfactants are generally, although not necessarily, compounds which include a carboxylate or phosphate group as the anion and an amino or quaternary ammonium moiety as the cation. These include, for example, various polypeptides, proteins, alkyl betaines, and natural phospholipids such as lecithins and cephalins. Other suitable solubilizing agents include Other suitable solubilizing agents (e.g., glycerin) may also be used, as will be appreciated by those skilled in the art. The solubilizing agent will be present in the range of approximately 0.01 wt. % to 40 wt. %, more preferably in the range of approximately 5.0 wt. % to 40 wt. %, and most preferably in the range of approximately 10.0 wt. % to 40 wt. %.

The urethral suppository will preferably, although not necessarily, be on the order of 2 to 20 mm, preferably 5 to 10 mm in length and less than about 5 mm, preferably less than about 2 mm in width. The weight of the suppository form will typically be in the range of approximately 1 mg to 100 mg, preferably in the range of approximately 1 mg to 50 mg. However, it will be appreciated by those skilled in the art that the size of the suppository can and will vary, depending on the potency of the drug, the nature of the formulation, and other factors.

In FIG. 1, a suitable transurethral drug delivery device is shown generally at 10. The device comprises a transurethral inserter 11 having an easily graspable segment 12 that has opposing symmetrically concave surfaces 13 and 14 adapted to be held by two fingers. The androgenic agent is contained within a urethral suppository (not shown) within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the transurethral drug delivery device shown in FIG. 1 represents a preferred device for use herein, again, it should be emphasized that a wide variety of device configurations and urethral dosage forms can be used.

Examples of other devices which may be used for transurethral drug administration are described and illustrated in WO 91/16021.

The devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

The method of drug delivery herein may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

The transurethral composition may contain one or more additional pharmacologically active agents, i.e., in addition to the androgenic agent. Vasoactive agents, particularly vasodilators, are preferred additional agents.

Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate ("SIN-1"), S-nitroso-N-acetyl-d,l-penicillamine ("SNAP"), S-nitroso-N-cysteine and S-nitroso-N-glutathione ("SNO-GLU"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone; naturally occurring prostaglandins such as $PGE_0$, $PGE_1$, $PGA_1$, $PGB_1$, $PGF_{1\alpha}$, 19-hydroxy-$PGA_1$, 19hydroxy-$PGB_1$, $PGE_2$, $PGA_2$, $PGB_2$, 19-hydroxy-$PGA_2$, 19-hydroxy-$PGB_2$, $PGE_3$, $PGF_3$,; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptides. Prazosin, prostaglandin $E_0$, prostaglandin $E_1$ and prostaglandin $E_2$ are particularly preferred vasoactive agents to be co-administered with the androgenic agent.

It may be desirable to deliver the androgenic agent in a urethral dosage form which provides for controlled or sustained release of the agent. In such a case, the dosage form comprises a biocompatible, biodegradable material, typically a biodegradable polymer. Examples of such polymers include polyester, polyalkylcyanoacrylate, polyorthoester, polyanhydride, albumin, gelatin and starch. As explained, for example, in PCT Publication No. WO 96/40054, these and other polymers can be used to provide biodegradable microparticles which enable controlled and sustained drug release, in turn minimizing the required dosing frequency.

The amount of active agent administered, and the dosing regimen used, will, of course, be dependent on the particular active agent selected, the age and general condition of the subject being treated, and the judgment of the prescribing physician. With transurethral administration, the daily dosage of active agent will be approximately half that of the dosage normally given in conjunction with other modes of administration. In general, transurethral administration of an androgenic agent for the present purpose involves a daily dosage of approximately 1.0 to 12.0 mg/day, preferably 3.0 to 12.0 mg/day. For testosterone, a typical daily dosage herein is in the range of approximately 1.0 to 8.0 mg/day.

Kits:

The invention also encompasses a kit for patients to carry out the aforementioned method. The kit contains the pharmaceutical composition to be administered, a device for administering the composition (i.e., a transurethral drug delivery device such as shown in FIG. 1), a container, preferably sealed, for housing the drug-containing composition and device during storage and prior to use, and instructions for carrying out drug administration in an effective manner, i.e., for administering the drug within the context of a dosage regimen for treating erectile dysfunction. The composition may consist of the drug in unit dosage form. The instructions may be in written or pictograph form, or can be on recorded media including audio tape, video tape, or the like.

Use in Conjunction with Venous Flow Control ("VFC") Device:

In an alternative embodiment of the invention, the pharmacologically active agent is administered in combination with a venous flow control device such as that described in commonly assigned U.S. patent application Ser. No. 08/782, 867, filed Jan. 16, 1997, entitled "Venous Flow Control Element for Maintaining Penile Erection." Preferred devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. Use of the VFC device also enables enhanced effectiveness of local drug therapy, in that the active agent is retained within the penis, allowing movement into the corpus cavernosa. This produces smooth muscle response and a consistent erectile response. In this embodiment, a kit will include the venous flow control device in addition to the components noted above, along with instructions for using the device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference.

EXAMPLE 1

Patients with a tendency toward vasculogenic impotence, are given 1.5 mg testosterone cypionate transurethrally every twelve hours. After several days to several weeks, various penile hemodynamic parameters are measured and compared with corresponding parameters evaluation prior to drug therapy. These parameters will typically include cavernosal artery peak systolic velocity, cavernosal artery end diastolic velocity, maximum arterial dilation, and pressure. Based on these measurements, a determination is made as to whether penile vascular sufficiency is present. It will be appreciated by those skilled in the art that any number of devices can be used to conduct the aforementioned measurements, providing that the desired level of accuracy is achieved. Duplex ultrasonography is the preferred mode of evaluating the penile hemodynamic parameters of interest. However, other types of techniques and equipment may be used as well, e.g., NMR spectroscopy, pressure cuffs, corpus cavernosograms, angiography, NPT (nocturnal penile tumescence) "Rigiscans," magnetic resonance imaging (MRI), computer aided tomography (CAT), pulsoximeters, and the like.

Examples of duplex ultrasonography devices which can be used in conjunction with the present method include those described in U.S. Pat. Nos. 4,334,543 to Fehr, 4,485,821 to Iinuma, and 4,612,937 to Miller, the disclosures of which are incorporated by reference herein. Suitable devices are available from a number of manufacturers, including, for example, Advanced Technology Laboratories (Bothell, Wash.) and Siemens Quantum (Issaquah, Wash.).

Based on the hemodynamic parameters measured using the aforementioned ultrasonography technique, a diagnosis can be made as to penile vascular sufficiency. Generally, if the measured PSV is less than about 50 cm/sec, more typically less than about 35 cm/sec, vascular inflow is insufficient, and a diagnosis of arterial insufficiency may be made. Alternatively, or additionally, if the measured EDV is greater than 0 cm/sec, more typically greater than about 5 cm/sec, a diagnosis of venous leakage may be made. It is expected that after the aforementioned drug therapy, the penile hemodynamic measurements which are conducted will lead to a finding of penile vascular sufficiency.

EXAMPLE 2

The procedure of Example 1 is repeated, except that drug is administered every six hours instead of every twelve hours, with dosage adjusted accordingly. Substantially the same results are expected.

EXAMPLE 3

The procedure of Example 1 is repeated, except that drug is administered every eight hours instead of every twelve hours, with dosage adjusted accordingly. Substantially the same results are expected.

EXAMPLE 4

The procedure of Example 1 is repeated, except that testosterone enanthate is substituted for testosterone cypionate. Substantially the same results are expected.

EXAMPLE 5

The procedure of Example 1 is repeated, except that testosterone propionate is substituted for testosterone cypionate. Substantially the same results are expected.

EXAMPLE 6

The procedure of Example 1 is repeated, except that methyltestosterone is substituted for testosterone cypionate. Substantially the same results are expected.

EXAMPLE 7

The procedure of Example 1 is repeated, except that a flexible, adjustable venous flow control device is used prior to and during sexual intercourse, on combination with the drug therapy described. Substantially the same results are expected.

EXAMPLE 8

Preparation of dosage forms: A pharmaceutical composition containing an androgenic agent for transurethral administration is prepared by mixing polyethylene glycol, molecular weight ($M_w$) approximately 4000, with an amount of testosterone sufficient to provide a total of 2.0 mg in the composition, and heating the mixture to a temperature just high enough to produce a drug-polymer melt. The mixture can then be poured into a mold suitable to provide a suppository approximately 5 mm in diameter and 12.5 mm in length, which is then allowed to cool. The suppository so provided is a unit dosage form suitable for transurethral administration. This procedure can be used with various other androgenic agents, PEGs, and additional components, e.g., enhancers or the like.

EXAMPLE 9

A penile insert coated with testosterone is prepared as follows. An ethylene vinyl acetate rod is formed into an insert having a shaft approximately 10 cm long with a spherical, blunted tip and a head portion approximately 4 mm thick and 1 cm in diameter on a hot plate. A dipping bath, comprising a 50—50 weight blend of PEG 1450 and PEG 400 and sufficient testosterone to provide for 2.0 mg in the total coating is prepared and heated to 70° C. The insert is suspended by its head, dipped into the dipping bath and removed. A penile insert suitable for transurethral administration of testosterone is thus provided.

I claim:

1. A method for treating erectile dysfunction, comprising administering to the urethra in need of such treatment a pharmaceutical composition comprising and androgenic agent selected from the group consisting of androsterone, dehydroepiandrosterone, testolactone, oxymetholone, and the pharmaceutically acceptable salts and esters, thereof, a vehicle suited to transurethral drug administration, and, optionally, a transurethral permeation enhancer, within the context of a dosing regimen which provides a dose of the agent effective to treat erectile dysfunction.

2. The method of claim 1, wherein the dosing regimen comprises administration of a daily dosage of approximately 1.0 to 12.0 mg androgenic agent.

3. The method of claim 2, wherein the agent is administered one to four times in a twenty-four hour period.

4. The method of claim 1, wherein the erectile dysfunction is vasculogenic impotence.

5. The method of claim 1, wherein drug administration is carried out by placing the androgenic agent at a depth of at least about 3 cm into the urethra.

6. The method of claim 1, wherein a transurethral permeation enhancer is administered with the androgenic agent.

7. The method of claim 1, wherein the pharmaceutical composition further comprises a vasoactive agent.

8. The method of claim 7, wherein the vasoactive agent is selected from the group consisting of antihypertensive agents, nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and combinations thereof.

9. The method of claim 1, wherein the pharmaceutical composition comprises a urethral suppository.

10. The method of claim 9, wherein the carrier is selected from the group consisting of water, silicone, waxes, petroleum jelly, polyethylene glycol, propylene glycol, liposomes and sugars.

11. The method of claim 10, wherein the carrier is polyethylene glycol.

12. The method of claim 1, further including application of a flexible, adjustable venous flow control device to the penis prior to and during sexual intercourse.

13. The method of claim 1, wherein the androgenic agent is androsterone.

14. The method of claim 1, wherein the androgenic agent is dehydroepiandrosterone.

15. The method of claim 1, wherein the androgenic agent is testolactone.

16. The method of claim 1, wherein the androgenic agent is oxymetholone.

17. A pharmaceutical composition for treating erectile dysfunction in a male individual, comprising a urethral suppository containing a therapeutically effective amount of an androgenic agent selected from the group consisting of androsterone, dehydroepiandrosterone, testolactone, oxymetholone, and the pharmaceutically acceptable salts and esters thereof, a suppository base suitable for transurethral drug administration comprising polyethylene glycol having a molecular weight in the range of approximately 200 and 2500, and, optionally, a transurethral permeation enhancer, wherein the therapeutically effective amount of the androgenic agent is such that the composition is effective to treat erectile dysfunction when administered transurethrally, and further wherein the suppository is approximately 2 to 20 mm in length and less than approximately 2 mm in length and less than approximately 2 in width.

18. The method of claim 17, herein the androgenic agent is androsterone.

19. The method of claim 17, wherein the androgenic agent is dehydroepiandrosterone.

20. The method of claim 17, wherein the androgenic agent is testolactone.

21. The method of claim 17, wherein the androgenic agent is oxymetholone.

22. A kit for treating erectile dysfunction in a male individual, comprising: a urethral suppository containing a therapeutically effective amount of an androgenic agent selected from the group consisting of androsterone, dehydroepiandrosterone, testolactone, oxymetholone, and the pharmaceutically acceptable salts and esters thereof, a suppository base suitable for transurethral drug administration comprising polyethylene glycol having a molecular weight in the range of approximately 200 and 2500, and, optionally, a transurethral permeation enhancer, wherein the therapeutically effective amount of the androgenic agent is such that the composition is effective to treat erectile dysfunction when administered transurethrally; a drug delivery means for administering the composition transurethrally; a container for housing the agent and drug delivery means; and written instructions for an individual to use the drug delivery means to carry out urethral drug administration in a manner effective to treat erectile dysfunction.

23. The method of claim 22, wherein the androgenic agent is androsterone.

24. The method of claim 22, wherein the androgenic agent is dehydroepiandrosterone.

25. The method of claim 22, wherein the androgenic agent is testolactone.

26. The method of claim 22, wherein the androgenic agent is oxymetholone.

* * * * *